US009932281B2

(12) United States Patent
Rothaemel

(10) Patent No.: US 9,932,281 B2
(45) Date of Patent: Apr. 3, 2018

(54) PROCESS AND PLANT FOR THE PRODUCTION OF OLEFINS

(71) Applicant: L'Air Liquide, Societe Anonyme pour l'Etude et l'Exploitation des Procedes Georges Claude, Paris (FR)

(72) Inventor: Martin Rothaemel, Frankfurt am Main (DE)

(73) Assignee: L'Air Liquide Société Anonyme Pour L'Étude Et L'Exploitation Des Procedes Georges Claude, Paris (FR)

(*) Notice: Subject to any disclaimer, the term of this patent is extended or adjusted under 35 U.S.C. 154(b) by 382 days.

(21) Appl. No.: 14/654,258

(22) PCT Filed: Dec. 3, 2013

(86) PCT No.: PCT/EP2013/075439
§ 371 (c)(1),
(2) Date: Jun. 19, 2015

(87) PCT Pub. No.: WO2014/095358
PCT Pub. Date: Jun. 26, 2014

(65) Prior Publication Data
US 2015/0353450 A1    Dec. 10, 2015

(30) Foreign Application Priority Data
Dec. 21, 2012 (DE) .................. 10 2012 112 840

(51) Int. Cl.
C07C 7/08 (2006.01)
C07C 1/20 (2006.01)
(Continued)

(52) U.S. Cl.
CPC ............... *C07C 7/08* (2013.01); *B01D 3/009* (2013.01); *B01D 3/14* (2013.01); *B01D 3/143* (2013.01);
(Continued)

(58) Field of Classification Search
CPC .. C07C 1/20; C07C 7/08; C07C 11/02; C07C 11/06; C07C 2521/04; C07C 2529/40;
(Continued)

(56) References Cited

U.S. PATENT DOCUMENTS 4,709,113 A    11/1987 Harandi et al.
2005/0101478 A1    5/2005 Janssen et al.
(Continued)

FOREIGN PATENT DOCUMENTS

DE    10 027 159    12/2001
DE    10 2005 048931    4/2007
DE    10 2011 014892    9/2012

OTHER PUBLICATIONS

International Search Report for PCT/EP2013/075439, dated Mar. 25, 2014.
(Continued)

Primary Examiner — Dirk Bass
(74) Attorney, Agent, or Firm — Justin K. Murray

(57) ABSTRACT

The present invention relates to a process for the production of olefins from oxygenates, comprising the following steps:
(i) heterogeneously catalyzed conversion of methanol to a product stream containing a $C_{3-}$ and a $C_{4+}$ fraction,
(ii) distillation of the product stream for separating the $C_{3-}$ fraction from a bottom product, and
(iii) distillation of the bottom product for separating a stream containing the $C_{4+}$ fraction and dimethyl ether from a stream containing water and methanol.

Furthermore, the invention also comprises a plant for carrying out this process.

7 Claims, 2 Drawing Sheets

(51) Int. Cl.
  *B01D 3/00* (2006.01)
  *B01D 3/14* (2006.01)
  *B01D 3/40* (2006.01)

(52) U.S. Cl.
  CPC .................. *B01D 3/40* (2013.01); *C07C 1/20* (2013.01); *C07C 2521/04* (2013.01); *C07C 2529/40* (2013.01)

(58) Field of Classification Search
  CPC .......... B01D 3/009; B01D 3/14; B01D 3/143; B01D 3/40
  USPC ............................................ 202/154; 203/29
  See application file for complete search history.

(56) References Cited

U.S. PATENT DOCUMENTS

| | | |
|---|---|---|
| 2006/0135632 A1 | 6/2006 | Lattner et al. |
| 2009/0178955 A1 | 7/2009 | Ryu |

OTHER PUBLICATIONS

Fielder, E., et al, Methonal-Process Technology, Sec. 5.4 and Fig. 5, pp. 1-25, Ullmann's Encyclopedia of Industrial Chemistry, Sixth Edition, 1998 Electronic Release.

Haag, S., et al, Methanol to Propylene—From Development to Commercialization, Reducing the Carbon Footprint of Fuels and Petrochemicals, DGMK Conference, Oct. 8-10, 2012, Berlin, Germany, 8pp.

Haag, S., et al, Methanol to Propylene—From Development to Commercialization, DGMK Conference, Oct. 8-10, 2012, Berlin, Germany, 19pp.

PROCESS AND PLANT FOR THE PRODUCTION OF OLEFINS

CROSS REFERENCE TO RELATED APPLICATIONS

This application is a § 371 of International PCT Application PCT/EP2013/075439, filed Dec. 3, 2013, which claims the benefit of DE102012112840.5, filed Dec. 21, 2012, both of which are herein incorporated by reference in their entireties.

TECHNICAL FIELD OF THE INVENTION

The present invention relates to the production of olefins, in particular propylene.

BACKGROUND

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process and the raw materials.

To obtain additional propylene, a number of processes exist, such as the PDH process which proceeds from propane as educt. What is known, however, above all is the so-called MTP process, in which olefins are produced from methanol (MeOH) or dimethyl ether (DME) by catalytic conversion on a zeolitic catalyst. By varying the catalyst under process conditions, the selectivity of the products obtained can be influenced and the product spectrum thus can be shifted towards short-chain olefins (then often also the process name Methanol-to-Olefin (MTO)), towards longer-chain products (then often also the process name Methanol-to-Gasoline (MTG)) or towards propylene.

The fundamentals of an MTP process are described for example in DE 10 2005 048 931 A1. From an educt mixture containing steam and oxygenates, such as methanol and/or dimethyl ether, $C_2$ to $C_4$ olefins are produced above all. By a heterogeneously catalyzed reaction in at least one reactor, the educt mixture is converted to a reaction mixture comprising low-molecular olefins and gasoline hydrocarbons. By a suitable separation concept, higher olefins, above all the $C_{5+}$ fraction, can at least partly be recirculated into the reactor as recycling stream and in said reactor for the most part be converted to propylene, whereby the propylene yield is increased.

One problem when carrying out the MTP process consists in that very pure oxygenates must be used as starting substances. When e.g. methanol is used as educt of the MTP reaction, this methanol must have a degree of purity of the specification AA, which means that the impurities must be smaller than 0.2‰. This mostly requires that in the plant for the production of methanol upstream of the MTP plant a very expensive purification method must be integrated. Usually, three distillation columns are used for this purpose (Ullmann's Encyclopedia of Industrial Chemistry, Sixth Edition, 1998 Electronic Release, METHANOL—Process Technology (Eckhard Fiedler, Georg Grossmann, Burkhard Kersebohm, Gunther Weiss, Claus Witte, section 5.4 and Fig. 5). In particular, the high energy costs incurred during the distillation distinctly lower the economy of the process.

In this connection, it is known from U.S. Pat. No. 4,709,113 that the feed of the MTP reactor can directly be guided into the reactor without particular purification. However, there is obtained a high amount of higher olefins, so that both a $C_5$-$C_8$ fraction and a $C_{9+}$ fraction is obtained and thus the yield of propylene in this process is distinctly lower and in addition the downstream purification method is very complex.

From US 2005/0101478 A1 it is known that when using molecular sieves as catalyst, oxygenates with a lower degree of purity can also be used. However, this method con-fines itself to describing the reaction control via the catalyst and does not discuss the purification of the product spectrum obtained or changes in its composition.

From US 2006/0135632 A1 finally an MTP process is known, in which methanol is pre-purified in a single purification stage and subsequently fed into the MTP reactor. After the conversion to olefins in the reactor, the entire product stream obtained is supplied to a quenching column From the same, a stream rich in olefins is withdrawn and the remaining aqueous stream is supplied to a second column. In this second separating column, the oxygenates are separated from the water contained in the stream, wherein the oxygenate-containing stream subsequently can be recirculated into the reactor. This concept has the disadvantage that directly subsequent to the reactor quenching is effected, i.e. the product stream coming from the reactor is cooled by adding water. The water content in the product stream is distinctly increased thereby. The high water contents which are present in both columns due to the proposed separation concept, however, lead to the fact that here as well very large amounts of energy are required for the purification, so that with an energy balance over the entire process the savings in the field of methanol purification hardly produce any effect or not at all.

SUMMARY OF THE INVENTION

Therefore, it is the object of the present invention to provide a process with which methanol with a low degree of purity can be used as educt for an MTP process, without the yield of propylene being reduced, and with which the energetic balance is distinctly improved at the same time.

In one embodiment, the process for producing olefins from oxygenates can include the following steps:
(i) heterogeneously catalyzed conversion of methanol to a stream containing a $C_{3-}$ and a $C_{4+}$ fraction,
(ii) distillation for separating the $C_{3-}$ fraction from a bottom product, and
(iii) distillation for separating a stream containing the $C_{4+}$ fraction and dimethyl ether from a stream containing water and methanol.

Thus, in the first distillation downstream of the reactor the desired valuable product, the $C_{3-}$ fraction, can be withdrawn already. The second column is switched such that the higher olefins are withdrawn together with dimethyl ether and parts of the contained methanol. Without an increase in the downstream purification and without influencing the product spectrum, the expensive methanol pre-purification thus can be omitted.

Furthermore, it was found to be favorable that the distillation for separating the $C_{3-}$fraction (process step (ii)) is carried out as extractive distillation, as the separation efficiency of the column thus is maximized.

According to an embodiment of the invention, methanol preferably is used as extracting agent within this distillation for separating the $C_{3-}$ fraction, as methanol already is contained as non-converted oxygenate in the stream supplied to the column, and thus only the quantity of the methanol to be separated is increased without introducing an additional substance into the process, which is to be recovered with great expenditure.

The process is designed particularly economic when in the distillation for separating a stream containing the $C_{4+}$ fraction and dimethyl ether from a stream containing water and methanol (process step (iii)) methanol, preferably with a degree of purity of less than 0.1 wt-%, water, preferably less than 0.05 wt-% water, particularly preferably less than 0.01 wt-% water is obtained via a side draw, and the methanol thus obtained is supplied to the column for separating the $C_{3-}$ fraction (process step (ii)) as extracting agent. Due to the arrangement of the two columns in the plant, this provides for a short conduit for the extracting agent and at the same time prevents that methanol with a lower degree of purity is used and thus an accumulation of impurities occurs.

In a preferred aspect, a partial stream of the methanol used as educt for the catalytic conversion is branched off and introduced into the distillation for separating a stream containing the $C_{4+}$ fraction and dimethyl ether (process step (iii)). This interconnection provides for both separating $C_4$ components from water and in parallel withdrawing a very pure methanol at one side draw in one and the same column, which methanol then is used as extracting agent in process step (ii). Due to this combination, the otherwise necessary purification of the methanol by three columns can be omitted, as a part of the methanol purification can also be performed in step (iii). In addition, the use of an externally supplied, possibly contaminated auxiliary substance for the extraction can be omitted.

Advantageously, the separated aqueous stream containing methanol from process step (iii) is subjected to a purification, so that the methanol and the water fraction are separated from each other. In a particularly favorable embodiment of the invention, the purified methanol is supplied to the heterogeneously catalyzed conversion in the reactor, whereby the turnover can be increased.

A further increase of the yield of the desired product propylene is obtained in that the stream containing $C_{4+}$ and dimethyl ether from process step (iii) likewise is supplied to the heterogeneously catalyzed conversion. The dimethyl ether is at least partly converted to olefins, while the longer-chain olefins for the most part are converted to propylene.

In principle, the process according to an embodiment of the invention can be carried out with methanol with a very high degree of purity, preferably degree AA, but is particularly effective when as educt methanol with a degree of purity of less than 99.8 wt-% (based on contained oxygenates, excluding the water content) is used, as the expensive methanol purification with a plurality of columns thus can be saved. In the process according to the invention a purification in only one distillation column usually will be effected, and the methanol then will directly be fed into the MTP reactor.

Certain embodiments of the invention furthermore also include a plant with the features as disclosed herein, which is suitable for carrying out the process with the features of the process as described herein. The plant for the production of olefins from oxygenates can include a reactor for the heterogeneously catalyzed conversion of methanol to a stream containing a $C_{3-}$ and a $C_{4+}$ fraction, a distillation column for separating the $C_3$ fraction from a bottom product, and a distillation column for separating a stream containing the $C_{4+}$ fraction and dimethyl ether from a stream containing water and methanol from the bottom product. Due to the novel purification, it is possible with this plant to also use methanol with a lower degree of purity, without the resulting product spectrum being shifted towards higher olefins or a higher energy demand being obtained.

Preferably, the distillation column for separating the $C_{3-}$ fraction and/or the distillation column for separating a stream containing the $C_{4+}$ fraction and dimethyl ether is a column for the extractive distillation. The separation efficiency of the respective column can distinctly be increased thereby.

In a particularly preferred aspect of the invention, the column for separating a stream containing the $C_{4-}$ fraction and dimethyl ether from a stream containing water and methanol includes a side draw by means of which methanol, preferably with a degree of purity of less than 0.1 wt-%, water, preferably less than 0.05 wt-% water, particularly preferably less than 0.01 wt-% water can be withdrawn. It hence is possible that the extracting agent required in the column for separating the $C_{3-}$ fraction is obtained within the column for separating a stream containing the $C_{4-}$ fraction and dimethyl ether.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
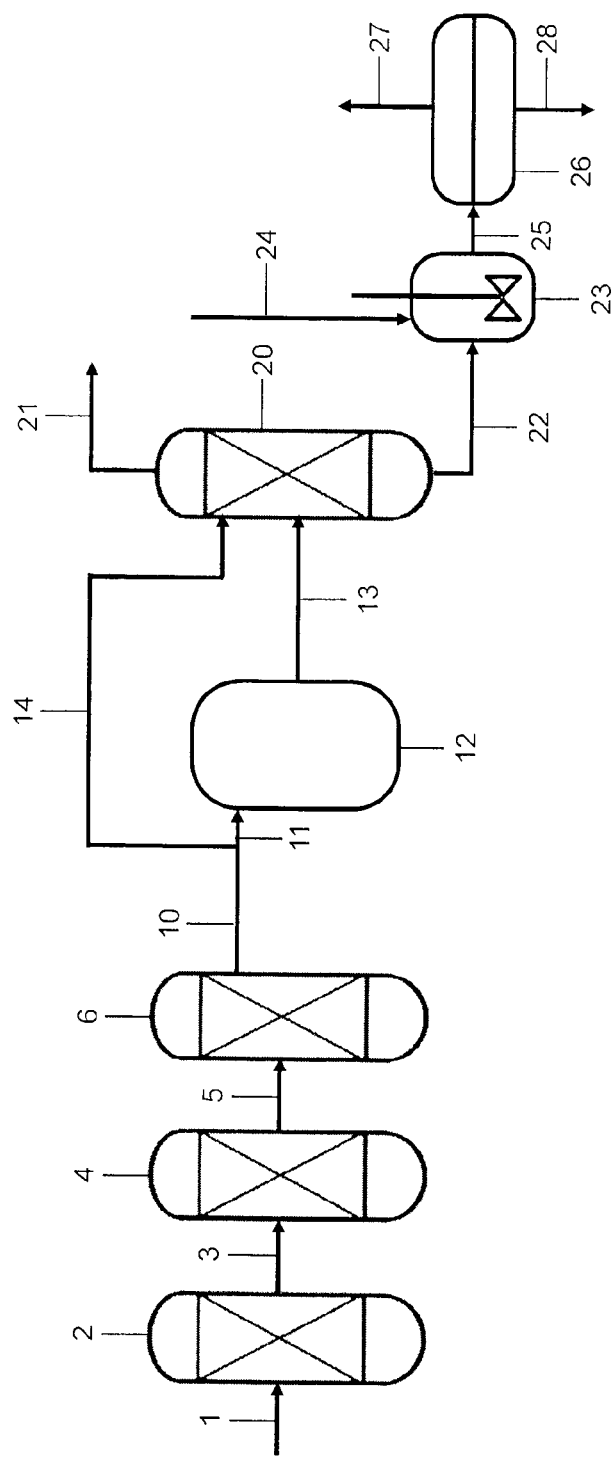
FIG. 1 shows an embodiment of the prior art.

Further features, advantages and possible applications of the invention can be taken from the following description of the drawings and the example. All features described and/or illustrated form the subject-matter of the invention per se or in any combination, independent of their inclusion in the claims or their back-references.

In the drawings:

FIG. 1 schematically shows a usual MTP process, and

Figure 2:
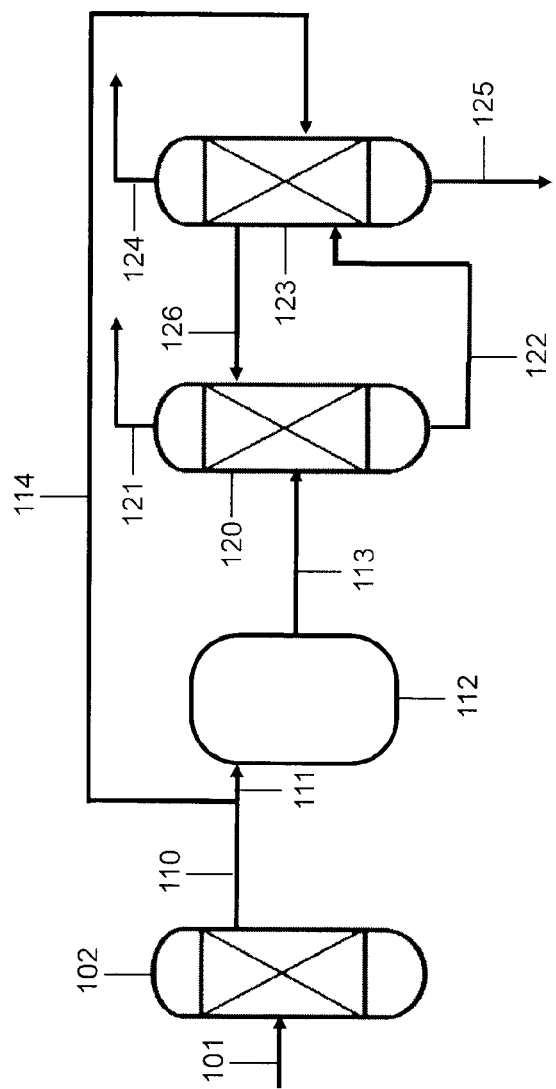
FIG. 2 shows an embodiment of the present invention.

FIG. 2 schematically shows the MTP process according to the invention.

FIG. 1 schematically shows the fundamental sequence of the combination of a standard methanol synthesis (Ullmann's Encyclopedia of Industrial Chemistry, Sixth Edition, 1998 Electronic Release, METHANOL—Process Technology (Eckhard Fiedler, Georg Grossmann, Burkhard Kersebohm, Gunther Weiss, Claus Witte, section 5.4 and Fig. 5) with an MTP process ("Methanol to Propylene: From Development to Commercialization" S. Haag, M. Rothaemel, S. Pohl, M. Gorny; Berlin, Oct. 10, 2012, DGMK Conference, 8-10, 10 2012, Berlin, Germany) (Crude methanol is fed into a distillation column 2 via conduit 1 and from there guided in purified form via conduit 3 into the next distillation column 4, where the methanol is purified further.) For the final purification, the methanol then is guided via conduit 5 into the distillation column 6, from which it is withdrawn with a degree of purity AA (degree of purity>99.85%).

Via conduits 10 and 11, the methanol subsequently gets into the MTP reactor 12, where it is converted to olefins. In general, the conversion inside the reactor is effected in an adiabatically operated dimethyl ether pre-stage, where the methanol is converted to dimethyl ether and water by using a highly active and highly selective alumina catalyst. The stream consisting of methanol, water and dimethyl ether then is supplied to the actual MTP reactor stage and mixed there with steam, wherein conversions of methanol and dimethyl ether of up to 99% can be achieved when using a suitable zeolite-based catalyst. The reaction also can be carried out in a single stage on a zeolite catalyst, preferably on a catalyst of the type ZSM-5. As occurring gross reaction equation, the following two main reactions take place:

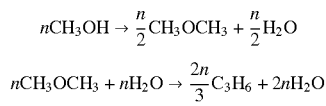

$$nCH_3OH \rightarrow \frac{n}{2}CH_3OCH_3 + \frac{n}{2}H_2O$$

$$nCH_3OCH_3 + nH_2O \rightarrow \frac{2n}{3}C_3H_6 + 2nH_2O$$

Of course, a number of side reactions take place, which lead to the formation of other olefins.

The entire product stream obtained subsequently is cooled and compressed and the gaseous fraction is supplied to a first separating means 20. The same preferably is operated as extractive distillation, wherein methanol is used as extracting agent. This methanol is branched off from the educt inflow 10 and introduced into the separating means 20 via conduit 14. Via conduit 21, the $C_{3-}$ fraction is withdrawn over the head of the separating means 20. The remaining bottom product, which contains the $C_{4+}$ fraction, methanol, dimethyl ether and water, is supplied via conduit 22 to a suitable extraction apparatus, e.g. a mixer-settler system 23, 26. In the mixer 23, water is added in addition and mixed with the bottom product of the column 20. Via conduit 25, this mixture is supplied to the settler 26 in which the organic phase separates from the aqueous phase. Via conduit 27, the organic stream substantially containing the $C_{4+}$ fraction thus can be obtained, wherein the same can be recirculated into the reactor 12 via a non-illustrated conduit, in order to there convert the higher olefins to the desired target product propylene.

Via conduit 28, the aqueous stream which also contains the oxygenates, above all dimethyl ether and methanol, is withdrawn. This stream must be subjected to a further purification. To increase the yield, it is recommendable to likewise guide the purified methanol and the dimethyl ether back into the reactor 12. It should be considered that in this purification, too, very high degrees of purity must be achieved, as the interconnection is not suitable for processing educts with a relatively low degree of purity.

FIG. 2 schematically shows a flow diagram of the configuration of the MTP process according to the invention. Via conduit 101, crude methanol is supplied to a single separating means 102, preferably a rectification. Depending on the reaction conditions in the methanol synthesis and the synthesis gas composition, the crude methanol contains 500-5000 wt.ppm of other oxygenates and about 3-30 wt-% of water. The methanol purified in the separating means 102 has a degree of purity of about 99.5% based on oxygenates and in addition contains between 3 and 30 wt-% of water depending on the reaction conditions in the methanol process and is fed into the reactor 112 via conduits 110 and 111.

In the reactor 112, the above-described MTP reaction takes place on a suitable catalyst, preferably a zeolitic system, particularly preferably a ZSM-5.

After cooling and compression, the reaction product obtained is supplied via conduit 113 to a separating device 120 in which the target product, the $C_{3-}$ fraction, is withdrawn over head. Via conduit 122, the bottom product consisting of the $C_{4+}$ fraction, methanol, dimethyl ether and water is supplied to the separating means 123.

The separating means 123 also is a distillation column. In this distillation column, the $C_{4+}$ fraction, dimethyl ether and in part also methanol, is withdrawn over head. Via a non-illustrated conduit, this top product can be recirculated into the reactor 112. In the reactor 112, the higher olefins for the most part are converted to olefins with shorter chain length, whereby the yield of propylene can be increased further. The recirculated dimethyl ether likewise is available for the conversion to olefins. The possibly contained methanol is the educt of the reaction and correspondingly is converted in the reactor 112. Such interconnection of the separating means is possible due to the invention, since the changed concept allows to also use recirculation streams with a lower degree of purity, so that here the dimethyl ether and methanol can be recycled together with the $C_{4+}$ fraction.

Via conduit 125, the bottom product which substantially consists of water and methanol is withdrawn from the column 123. From this aqueous stream, the methanol can be removed in a non-illustrated way and likewise be recirculated into the reactor 112. Oxygenates contained in the crude methanol therefore do not disturb, since they (except for DME) boil higher than propylene. They are thus obtained in the bottom of column 120 and are removed by conduit 122 in column 123 via conduit 125.

Advantageously, the column 120 is formed as extractive distillation. As extracting agent for the column 120 methanol with a high degree of purity (<0.1% water) is used, which is withdrawn via a side draw of the separating means 123 and guided into the column 120 via conduit 126. Due to the described interconnection of the columns, methanol can be produced directly in the process in the high purity necessary for the extractive distillation in column 120, so that the previously necessary purification of the entire methanol feed stream in three columns provided for this purpose can be omitted.

EXAMPLE

The following example shows the composition of the streams when using the process according to the invention, as it is shown in FIG. 2. The mass flow rate is 1000 kg/h.

The two columns 120 and 123 have the following specifications:

Column 120 has 30 trays and a reflux ratio of 4.6. The draw of the bottom product is effected in tray 15, the feeding of the extracting agent methanol in tray 2, wherein the trays each are to be counted from the top.

Column 123 has 25 trays and a reflux ratio of 2.0. The extracting agent crude methanol is fed into tray 20, while the inflow from column 120 is fed into tray 7, wherein the trays each are to be counted from the top.

For the mass balance the following values are obtained:

TABLE 1

Mass balance of the process according to FIG. 2

| | Stream 114 | Stream 113 | Stream 121 | Stream 124 | Stream 125 | Stream 126 |
|---|---|---|---|---|---|---|
| Methanol | 956.1 | | 0.0 | 874.2 | 82.2 | 816.2 |
| Ethanol | 0.24 | 0.40 | 0.00 | 0.02 | 0.62 | 0.18 |
| Propanol | 0.007 | | 0.000 | 0.000 | 0.007 | 0.000 |
| C2 = | | 725.1 | 725.1 | 0.0 | 0.0 | 0.0 |
| C3 = | | 2925.5 | 2896.5 | 29.0 | 0.0 | 0.4 |
| C2 | | 10.2 | 10.19 | 0.0 | 0.0 | 0.0 |

TABLE 1-continued

Mass balance of the process according to FIG. 2

|  | Stream 114 | Stream 113 | Stream 121 | Stream 124 | Stream 125 | Stream 126 |
|---|---|---|---|---|---|---|
| C3 |  | 71.0 | 50.72 | 20.6 | 0.0 | 0.7 |
| i-C4 |  | 3019.9 | 1.749 | 3017.9 | 0.0 | 128.9 |
| n-C4 |  | 545.6 | 0.025 | 545.6 | 0.0 | 4.5 |
| i-C4 = |  | 508.6 | 0.053 | 508.6 | 0.0 | 5.0 |
| 1-C4 = |  | 565.1 | 0.123 | 564.9 | 0.0 | 36.4 |
| c2C4 = |  | 508.6 | 0.208 | 508.4 | 0.0 | 24.1 |
| tr2C4 = |  | 788.2 | 0.210 | 787.9 | 0.0 | 44.7 |
| Water | 43.6 |  | 0.000 | 0.000 | 43.6 | 0.033 |
| DME |  | 309.3 | 0.906 | 308.4 | 0.0 | 7.2 |
| M-formates |  | 8.2 | 0.000 | 8.2 | 0.0 | 0.327 |
| Acetone | 0.008 | 14.2 | 0.000 | 14.2 | 0.0 | 4.6 |
| MEK | 0.005 |  | 0.000 | 0.0 | 0.0 | 0.0 |

LIST OF REFERENCE NUMERALS 1 conduit
2 separating means
3 conduit
4 separating means
5 conduit
6 separating means
10, 11 conduit
12 reactor
13, 14 conduit
20 separating means
21, 22 conduit
23 mixer
24, 25 conduit
26 settler
27, 28 conduit
101 conduit
102 separating means
110, 111 conduit
112 reactor
113, 114 conduit
120 separating means
121, 122 conduit
123 separating means
124-126 conduit While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A process for producing olefins from oxygenates, the process comprising the following steps:
   (i) heterogeneously catalyzed conversion of methanol to a product stream containing a $C_{3-}$ and a $C_{4+}$ fraction;
   (ii) distillation of the product stream for separating the $C_{3-}$ fraction from a bottom product in a first distillation column, wherein the distillation in step (ii) is an extractive distillation in which an extracting agent is used, wherein the extracting agent is methanol; and
   (iii) distillation of the bottom product for separating a top stream containing the $C_{4+}$ fraction and dimethyl ether from a bottom stream containing water and methanol in a second distillation column,
   wherein the methanol used as the extracting agent in step (ii) is obtained via a side draw of methanol sourced from step (iii).

2. The process according to claim 1, wherein a partial stream of the methanol used for the heterogeneously catalyzed conversion is branched off and introduced into the process step (iii).

3. The process according to claim 1, wherein the stream containing water and methanol, which is obtained from process step (iii), is subjected to a purification in which purified methanol is separated.

4. The process according to claim 3, wherein the purified methanol is recirculated into the heterogeneously catalyzed conversion.

5. The process according to claim 1, wherein the stream containing the $C_{4+}$ fraction and dimethyl ether, which is obtained in process step (iii), is recirculated into the heterogeneously catalyzed conversion.

6. The process according to claim 1, wherein methanol with a degree of purity <99.8 wt-% is used as educt, wherein the wt-% is based on contained oxygenates, excluding the water content.

7. A plant for the production of olefins from oxygenates, the plant comprising:
   a reactor configured to convert methanol, via heterogeneous catalization, to a product stream containing a $C_{3-}$ and a $C_{4+}$ fraction;
   a first distillation column configured to separate the product stream into the $C_{3-}$ fraction and a bottom product, wherein the first distillation column is an extractive distillation column;
   a second distillation column configured to separate the bottom product from the first distillation column into a top stream containing the $C_{4+}$ fraction and dimethyl ether and a bottom stream containing water and methanol; and a side draw conduit in fluid communication with the first distillation column and the second distillation column, wherein the side draw conduit is configured to provide methanol from the second distillation column to the first distillation column, such that the provided methanol is used as an extracting agent within the first distillation column.

* * * * *